United States Patent
Trerotola (10) Patent No.: US 6,776,770 B1
(45) Date of Patent: Aug. 17, 2004

(54) THROMBOASPIRATION VALVE-FILTER DEVICE AND METHODS

(75) Inventor: Scott O. Trerotola, Indianapolis, IN (US)

(73) Assignee: Advanced Research & Technology Institute, Indianapolis, IN (US)

(*) Notice: Subject to any disclaimer, the term of this patent is extended or adjusted under 35 U.S.C. 154(b) by 340 days.

(21) Appl. No.: 09/657,300

(22) Filed: Sep. 7, 2000

(51) Int. Cl.⁷ .................... A61M 37/00; B01D 33/00
(52) U.S. Cl. .............. 604/6.09; 604/6.1; 604/6.11; 210/416.1
(58) Field of Search ............. 604/4.01, 5.01, 604/6.09, 6.1, 6.11, 8, 9; 210/348, 416.1, 418, 420, 500.21; 606/191, 194, 198, 200

(56) References Cited

U.S. PATENT DOCUMENTS

| | | | |
|---|---|---|---|
| 3,946,731 A | 3/1976 | Lichtenstein | |
| 4,817,600 A | 4/1989 | Herms et al. | |
| 4,832,055 A | 5/1989 | Palestrant | |
| 4,957,501 A | 9/1990 | Lahille et al. | |
| 5,234,403 A | 8/1993 | Yoda et al. | |
| 5,279,546 A | 1/1994 | Mische et al. | |
| 5,329,942 A | 7/1994 | Gunther et al. | |
| 5,368,034 A | 11/1994 | Isner | |
| 5,370,657 A | 12/1994 | Irie | |
| 5,380,299 A | 1/1995 | Fearnot et al. | |
| 5,419,774 A | 5/1995 | Willard et al. | |
| 5,458,574 A | 10/1995 | Machold et al. | |
| 5,531,788 A | * 7/1996 | Dibie et al. ............... 606/158 |
| 5,536,412 A | 7/1996 | Ash | |
| 5,554,117 A | * 9/1996 | Ensminger et al. ......... 604/175 |
| 5,562,698 A | 10/1996 | Parker | |
| 5,601,595 A | 2/1997 | Smith | |
| 5,607,579 A | 3/1997 | Latham, Jr. et al. | |
| 5,626,605 A | 5/1997 | Irie et al. | |
| 5,681,347 A | 10/1997 | Cathcart et al. | |
| 5,702,368 A | 12/1997 | Stevens et al. | |
| 5,713,849 A | 2/1998 | Bosma et al. | |
| 5,725,552 A | 3/1998 | Kotula et al. | |
| 5,746,767 A | 5/1998 | Smith | |
| 5,800,457 A | 9/1998 | Gelbfish | |
| 5,827,229 A | 10/1998 | Auth et al. | |

(List continued on next page.)

OTHER PUBLICATIONS

J. Brossmann, MD and J.J. Bookstein, MD, "Percutaneous Balloon–Assisted Thrombectomy: Preliminary In Vivo Results With an Expandable Vascular Sheath System", Radiology, vol. 206, No. 2, pp. 439–445 (Feb., 1998).

S. Muller–Hulsbeck, H. Schwarzenberg, C. Bangard, J.C. Steffens, and M. Heller, "Vacuum Pump Controlled Aspiration Thrombectomy: In Vitro Comparison With a Thrombus Fragmentation Procedure" (translation), Fortschr. Rontgenstr., vol. 168, No. 2, pp. 191–194 (1998).

Guy S. Reeder, MD. et al., "Aspiration Thrombectomy for Removal of Coronary Thrombus," The American Journal of Cardiology, p. 107–110, (Jul. 1, 1992).

(List continued on next page.)

Primary Examiner—Angela D. Sykes
Assistant Examiner—Leslie R. Deak
(74) Attorney, Agent, or Firm—Dann, Dorfman, Herrell & Skillman, PC.

(57) ABSTRACT

A device and methods for filtering blood clot particles from blood from patient undergoing treatment for a thrombotic condition with a catheter are described. The device comprises a housing having a first end defining a fluid port, an opposite end defining a suction port, and a valve member disposed between the fluid port and the reservoir. The valve member has a semipermeable membrane portion permeable to blood but impermeable to blood clot particles and a one way valve portion having an open position permitting passage of fluid and particles from the fluid port to the reservoir and a closed position blocking passage of particles between the reservoir and the fluid port.

13 Claims, 5 Drawing Sheets

U.S. PATENT DOCUMENTS

| | | | | |
|---|---|---|---|---|
| 5,858,238 A | | 1/1999 | McRea et al. | |
| 5,925,063 A | * | 7/1999 | Khosravi | 606/200 |
| 5,938,645 A | | 8/1999 | Gordon | |
| 6,010,531 A | | 1/2000 | Donlon et al. | |
| 6,059,745 A | * | 5/2000 | Gelbfish | 604/6.09 |
| 6,120,474 A | * | 9/2000 | Okuda et al. | 210/446 |
| 6,146,396 A | | 11/2000 | Konya et al. | |
| 6,161,547 A | | 12/2000 | Barbut | |
| 2001/0049486 A1 | | 12/2001 | Evans et al. | |

OTHER PUBLICATIONS

F. Poulain et al., "Local Thombolysis and Thromboaspiration in the Treatment of Acutely Thrombosed Arteriovenous Hemodialysis Fistulas," Cardio Vascular and Interventional Radiology, Spinger–Verlag New York Inc., p. 98–101. (1991).

Hans–Joachin Wagner et al., "Long–Term Results of Percutaneous Aspiration Embolectomy," Cardio Vascular and Interventional Radiology, Springer–Verlag New York Inc., vol. 17, p. 241–246, (1994).

Erhard E. Starck, M.D. et al., "Percutaneous Aspiration Thromboembolectomy," Radiology, p. 61–66, (Jul. 1985).

Rolf W. Guenther, MD et al., "Aspiration Catheter for Percutaneous Thombectomy: Clinical Results1," Radiology, vol. 175 (No. 1), p. 271–273, (1990).

Melhem J.A. Sharfuddin, MD et al., "Percutaneous Balloon–assisted Aspiration Thombectomy of Clotted Hemo–dialysis Access Grafts1," Journal of Vascular and Interventional Radiology, vol. 7 (No. 1), p. 177–183, (1996).

Luc Turmel–Rodrigues, MD et al., "Manual Thomboaspiration and Dilation of Thombosed Dialysts Access: Mid–term Results of a Simple Concept1," Journal of Vascular and Interventional Radiology, vol. 8 (No. 5), p. 813–824, (1997).

Tatsuaki Murakami, MD et al., "Intracoronary Aspiration Thrombectomy for Acute Myocardial Infarction," The American Journal of Cardiology, Excerpia Medica, Inc., vol. 82, p. 839–844 (Oct. 1, 1998).

Jacob Shani, MD et al., "Mechanical Manipulation of Thrombus: Coronary Thrombectomy, Intracoronary Clot Displacement, and Transcatheter Aspiration," The American Journal of Cardiology, vol. 72, p. 116G–118G, (Dec. 16, 1993).

Mark Dooris, MBBS et al., "Successful Reversal of Cardiogenic Shock Precipitaed by Saphenous Vein Graft Distal Embolization Using Aspiration Thombectomy," Catherization and Cardiovascular Diognosis, Wiley–Liss, Inc., vol. 33, p. 267–271, (1994).

S. Mitchell Rivitz et al., "Percutaneous Aspiration Thrombectomy of an Acutely Occluded Aortorenal Bypass Graft," Interventional Radiology Case Conference Massachesetts General Hospital, American Journal of Radiology, p. 455–458, (1995).

Letter to Editor regarding article entitled, "Percutaneous Aspiration Thomboembolectomy", written by Klaus Rauber, MD.

* cited by examiner

THROMBOASPIRATION VALVE-FILTER DEVICE AND METHODS

FIELD OF THE INVENTION

The present invention generally relates to the treatment of thrombotic conditions and more specifically to devices and methods for salvaging or recovering blood to reduce net blood loss during procedures and as a result improve the safety of these procedures for health care workers and patients.

BACKGROUND OF THE INVENTION

Some of the current medical treatments of thrombotic conditions such as arterial emboli and thrombosis, deep vein thrombosis and pulmonary thromboembolic disease often require the aspiration of clot fragments following their mechanical fragmentation with one of several devices. In the process of removing these clot fragments, moderate to large amounts of blood can be aspirated along with the clot fragments. Obviously, keeping blood loss to minimum is important in any surgical procedure but it is particularly important in this setting because of the frequently associated concurrent illnesses. In addition, blood loss could be a factor limiting the success of the procedure unless the blood can be returned to the patient in someway.

Turmel-Rodrigues, et al. advocated filtering aspirated blood through a gauze sponge with reinjection of the blood with no adverse sequelae. (Manual thromboaspiration and dilation of thrombosed dialysis access: mid-term results of a simple concept. JVIR 1997, 8:813–824). During this procedure, the blood containing clot fragments are withdrawn from the thrombus area with a 50 mL syringe. Then, the removed blood is squirted through a gauze sponge into a cup, aspirated back into a syringe, and reinjected into the patient. Although this blood filtration process reduces blood loss, it has many drawbacks. First, a substantial amount of blood is absorbed into the sponge. Second, the additional filtration steps prolong the overall thromboaspiration procedure time. Thirdly, the prolonged procedure time creates a risk of overexposure to x-ray to the operators whose hands are working close to fluoroscopy. Id. Finally, the filtration procedure involves handling the blood, which creates additional risk of infection for the patient and contamination for the health care worker.

At present, there are many complex devices available for use in major surgical procedures, trauma and other settings of uncontrolled blood loss. None of these are suitable for salvaging blood during thromboaspiration procedures. For example, the apparatus disclosed in U.S. Pat. No. 5,858,238 to McRea et al. is designed for salvaging blood from a patient and selective removing water, fluids, and low molecular weight solutes in the blood. The apparatus has several connecting parts that perform these functions in a complicated blood treatment process.

Other devices relating to the removal of blood clot fragments from the blood stream include those for use in intravascular treatments, especially in patients with deep vein thrombosis conditions. These devices include filters or valves that can be implanted inside a patient to filter particulate matter from a fluid flow or to regulate the fluid flow. For example, U.S. Pat. No. 5,800,457 to Gelbfish discloses an intravascularly deployable filtration device in a conical shape. This particular device has an access port which functions as a coupling element with a distal end of an elongated debris removal instrument. The design of this device allows for the blood clot particles to be trapped on the passive filter system. The clot particles can be removed by the debris removal instrument without having to remove the filtration device itself. Additionally, U.S. Pat. No. 5,925,063 to Khosravi describes an apparatus deployable within a body vessel or organ that can function as a filter or a valve. This apparatus has a plurality of flaps comprising a fluid permeable mesh that can be configured to project toward one another and overlap each other to form a filter. The plurality of flaps can also comprise a resilient material capable of defecting and form a valve that opens when a pressure differential across the flaps exceeds a predetermined valve.

Although the aforementioned devices can be used for blood filtration, they are indicated for a long-term intravascular treatment, which requires implantation and removal of the device during surgical procedures. These devices do not satisfy the need for extracorporeal blood treatment associated with thromboaspiration procedures.

A need has remained for devices and methods for filtering blood clot particles from blood, salvaging the filtered blood, and quickly returning the filtered blood to the patient.

A need has also remained for blood filter devices that are disposable, inexpensive and easy to operate.

SUMMARY OF THE INVENTION

Briefly describing one aspect of the invention, a device for filtering blood clot particles from blood is provided. The device includes a housing having a first end defining a fluid port and an opposite end defining a suction port. The fluid port is engagable to the side arm of a catheter that is used to withdraw blood from a patient. The housing further defines a reservoir in fluid communication with the fluid port. A valve member is disposed between the fluid port and the reservoir. The valve member has a semipermeable membrane portion permeable to blood and impermeable to blood clot particles. The valve member is further provided with a one way valve portion having an open position permitting passage of fluid and particles from the fluid port to the reservoir and a closed position blocking passage of particles between the reservoir and the fluid port.

In one specific embodiment, the device has a valve member that includes at least one leaflet composed of a resilient material capable of: deflecting to achieve the open position upon receiving suction pressure from the suction port and returning to the closed position when suction is removed.

In another specific embodiment, the valve member includes a plurality of valvate leaflets, each composed of a resilient material capable of deflecting to the open position and returning to the closed position.

In yet another aspect, the housing comprises a first housing portion and a second housing portion. The first housing portion includes the first end defining a fluid port and an opposite end defining a first opening. The first housing portion further defines a chamber in fluid communication with the fluid port and the first opening. The second housing portion has a first end defining the suction port and an opposite end defining a second opening. The second housing portion further defines the reservoir, which is in fluid communication with the suction port and the second opening. The opposite end of the second housing portion is hermetically sealingly engagable to the opposite end of the first housing portion.

In preferred embodiments, a first engagement member is disposed on the opposite end of the first housing portion and a second engagement member is disposed on the opposite end of the second housing portion. The first engagement member is matable with the second engagement member to releasably secure the housing portions together. In one embodiment, the engagement members are screw threads.

In yet another aspect, the engagement member is a hinge hingedly connecting the first housing portion to the second housing portion and a lock member releasingly engaging the first housing portion to the second housing portion.

The invention further provides methods for filtering blood clot particles from blood of a patient undergoing treatment for a thrombotic condition. The methods include: providing a catheter having a side arm port for suction and introducing the catheter into a blood vessel, engaging the fluid port of a device of this invention to the side arm port of the catheter, applying suction pressure to the suction port of the device to open the valve and draw blood containing blood clot particles through the catheter, past the valve and into the reservoir, and then removing the suction pressure to close the valve and trap particles in the reservoir.

In yet another embodiment, the methods include the step of reinjecting the blood from the reservoir into the patient through the catheter. The invention contemplates repeating the steps until the blood clot particles are removed. The methods also include disengaging the first housing portion from the second housing portion, removing blood clot particles from the valve, and then re-engaging the first housing portion to the second housing portion.

Accordingly, it is one object of the invention to provide devices and methods for safely salvaging blood to reduce net blood loss during treatment for thrombotic disorders. This and other objects, advantages and features are accomplished according to the devices and methods of the present invention.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention that would normally occur to one skilled in the art to which the invention relates.

The present invention provides devices and methods for filtering blood clot particles from blood from a patient undergoing treatment for a thrombotic condition. The device is elegant in construction, economical, and easy to assemble and use. The methods allow the blood to be salvaged, filtered and returned to the patient quickly. The present invention promotes the safety of both the patient and the operator.

Figure 1:
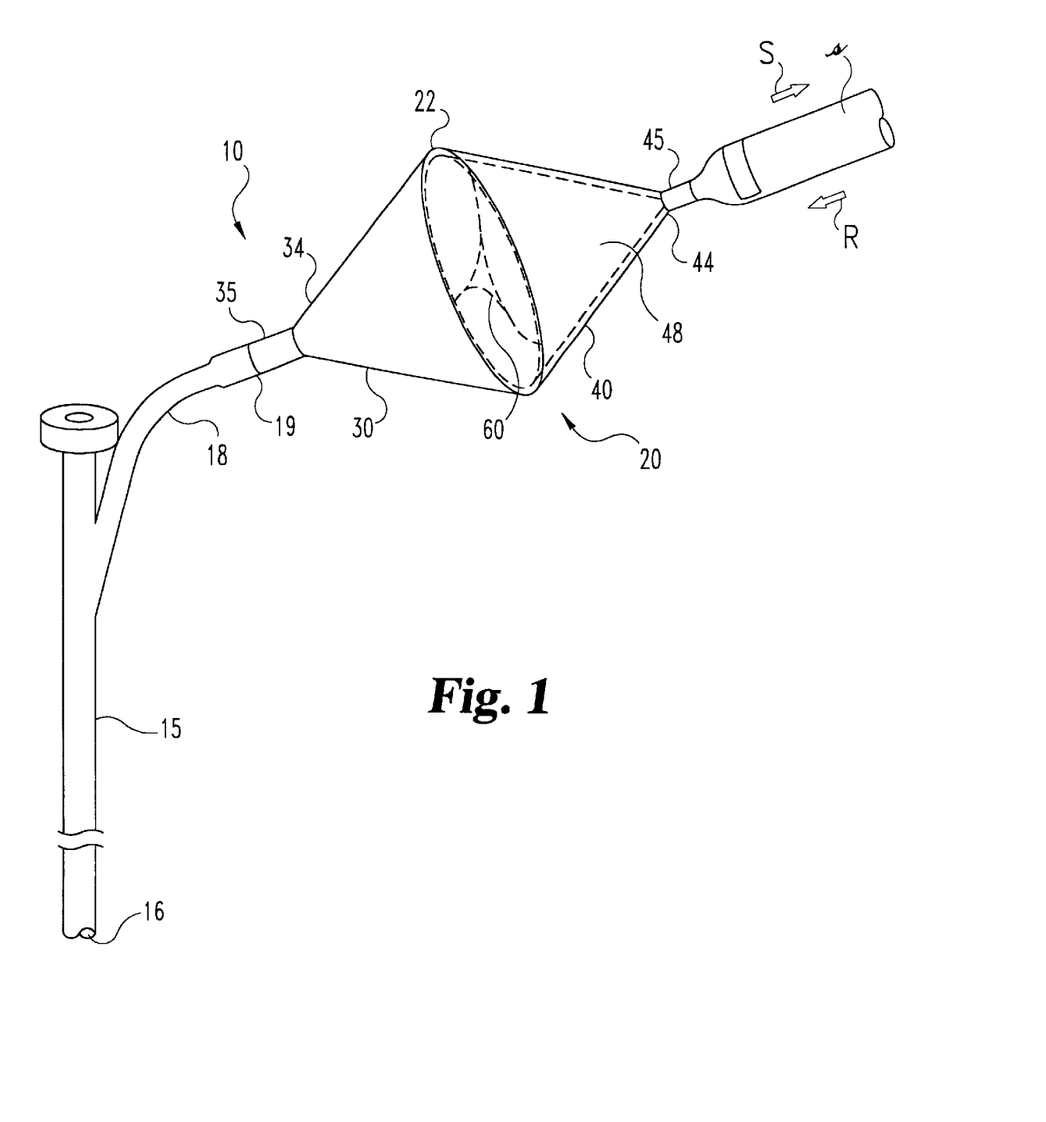
FIG. 1 is a side elevational view of an assembly according to one embodiment of this invention.

An assembly 10 according to one embodiment of this invention is shown in FIG. 1. The assembly is provided for filtering blot clot particles from blood from a patient undergoing treatment for a thrombotic condition, such as arterial emboli and thrombosis, deep vein thrombosis and pulmonary thromboembolic disease. Assembly 10 includes a catheter 15 defining a primary lumen (not shown) and having a first end 16 that is insertable into a blood vessel (not shown) near a blood clot within the vessel. The term catheter is used herein to mean generally any of the various devices that can be used to address a thrombotic disorder, such as deep vein thrombosis, including but not limited to a standard vascular introducer sheath with a high flow side arm. Side arm 18 has a suction lumen (not shown) in fluid communication with the primary lumen as is known in the art. Such catheters are typically used by applying suction to end 19 to remove blood clot particles along with blood.

Assembly 10 includes a device 20 for filtering and salvaging the removed blood. Device 20 includes a housing 22 having a first end 34 defining a fluid port 35 that is engagable to the end 19 of the side arm 18 of catheter 15 and an opposite end 44 defining a suction port 45. In one specific embodiment, the fluid port 35 is a large bore male Luer type adaptor that is configured in luminal dimension to securely engage the end 19 of the side arm 18 of the catheter 15. The suction port 45 in a specific embodiment is a female Luer type adaptor to which a standard syringe or other device can be attached to provide suction.

Figure 2:
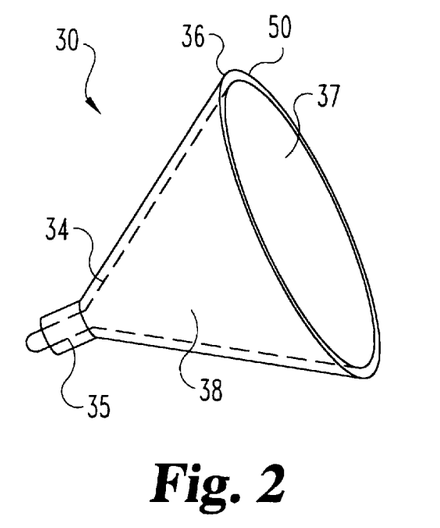
FIG. 2 is a side perspective view of a first housing portion according to one embodiment of this invention

In the particular embodiment shown in FIG. 1, housing 22 includes first and second housing portions 30, 40. First housing portion 30 includes the first end 34 defining the fluid port 35 and an opposite end 36 defining a first opening 37 as shown more clearly in FIG. 2. First housing portion 30 further defines a chamber 38 in fluid communication with the fluid port 35 and first opening 37.

Figure 3:
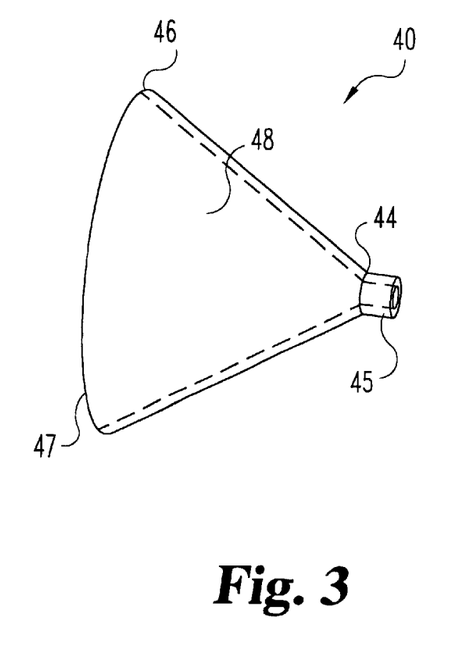
FIG. 3 is a side elevational view of a second housing portion according to one embodiment of this invention.

Second housing portion 40 includes a first end 44 defining a suction port 45 and an opposite end 46 defining a second opening 47 as shown more clearly in FIG. 3. Second housing portion 40 defines a reservoir 48 in fluid communication with the suction port 45 and the second opening 47. A syringe or other suitable means is used to create suction pressure in direction of arrow S.

The opposite end 46 of the second housing portion 40 is hermetically sealingly engagable to the opposite end 36 of the first housing portion 30. Any suitable means for hermetically sealingly engaging the opposite ends 36, 46 is contemplated. For example, a seal ring 50 may be disposed between the housing portions 30, 40 or the housing portions may be integrally formed into a single housing. In the embodiment shown in FIG. 2, seal ring 50 is shown disposed at the opposite end 36 of first housing portion 30.

Referring again to FIG. 1, device 10 includes a valve member 60 disposed between the fluid port 35 and the reservoir 48. In the preferred embodiment shown in FIG. 4, valve 60 is fitted into the opposite end 36 of first housing portion 30. The valve members of this invention include a semipermeable membrane portion that is permeable to blood but impermeable to blood clot particles. The valve members further include a valve portion having an open position permitting passage of fluid and particles from the fluid port to the reservoir and a closed position blocking passage of particles between the reservoir and the fluid port. As such, the valve portion is a two-way valve for blood and a one-way valve for blood clots and blood clot particles.

The semipermeable membrane portion is composed of any suitable material that is biocompatible, has appropriate stiffness and flexibility, and is permeable to blood but impermeable to blood clots and blood clot particles. The membrane could be composed of one of the following materials that has been manufactured to the requirements of this invention: porous polyethylene, cellulose diacetate, polycarbonate, polyvinylchloride, polymethylmethacrylate, polyethylene and polyethylenevinylalocohol. For example, the membrane portion might be a medical grade mesh material with a pore size between about 0.01 mm and about 1.0 mm. In a preferred embodiment, the pore size of the membrane is similar to the pore size of standard gauze sponge materials that are commercially available to health care workers.

Preferably, the valve member includes at least one leaflet composed of a resilient material capable of: deflecting to achieve the open position upon receiving suction pressure from the suction port and returning to the closed position when suction is removed. In the preferred embodiment shown in FIGS. 1, 4 and 5, the valve member 60 includes a plurality of valvate leaflets 61, 62, 63 that resemble the valves of a human heart. Although FIGS. 4 and 5 show three leaflets, the invention contemplates any suitable number of leaflets.

Figure 4:
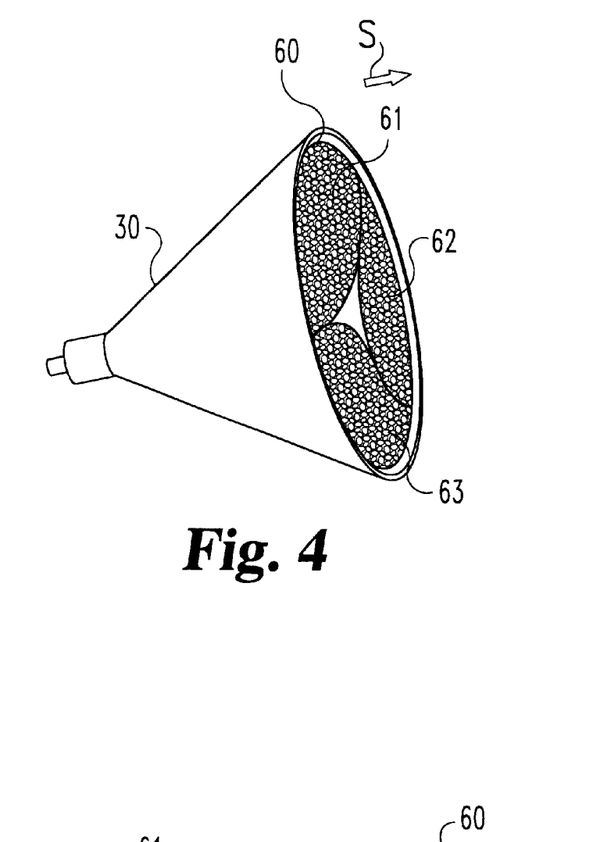
FIG. 4 is a side perspective view of a first housing portion with a valve of this invention.
Figure 5:
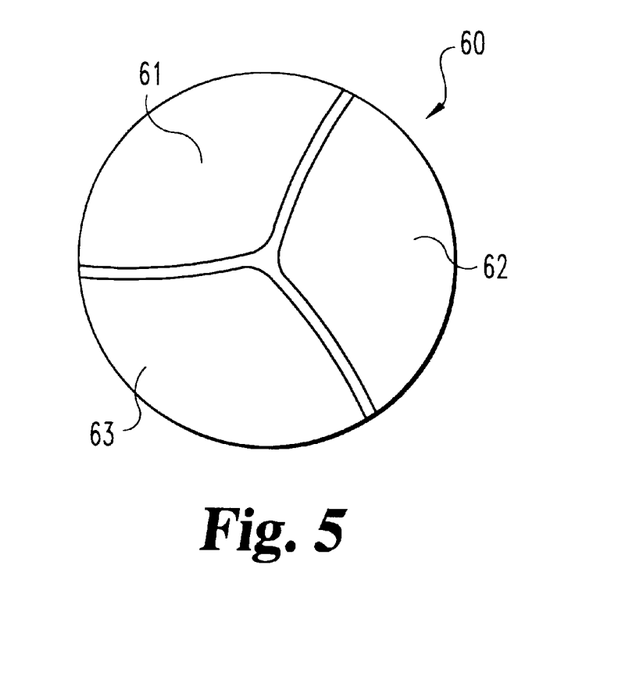
FIG. 5 is an end elevational view of a valve of this invention.

In the particular embodiment shown in FIGS. 1, 4 and 5, each leaflet 61, 62, 63 is composed of a semipermeable membrane material, which is also a resilient material capable of deflecting to achieve the open position. Leaflets 61, 62, 63 are disposed circumferentially adjacent to one another from an interior surface of either the first housing portion 30 or the second housing portion 40. Leaflets 61, 62, 63 are deformable from the closed position to the open position in which their tips or ends 61', 62', 63' are deflected toward the direction of the suction force S. When first housing portion 30 is engaged to second housing portion 40, the tips 61', 62', 63' are deflected towards the reservoir to the open position as shown in FIG. 4 upon application of the suction force S.

Figure 6:
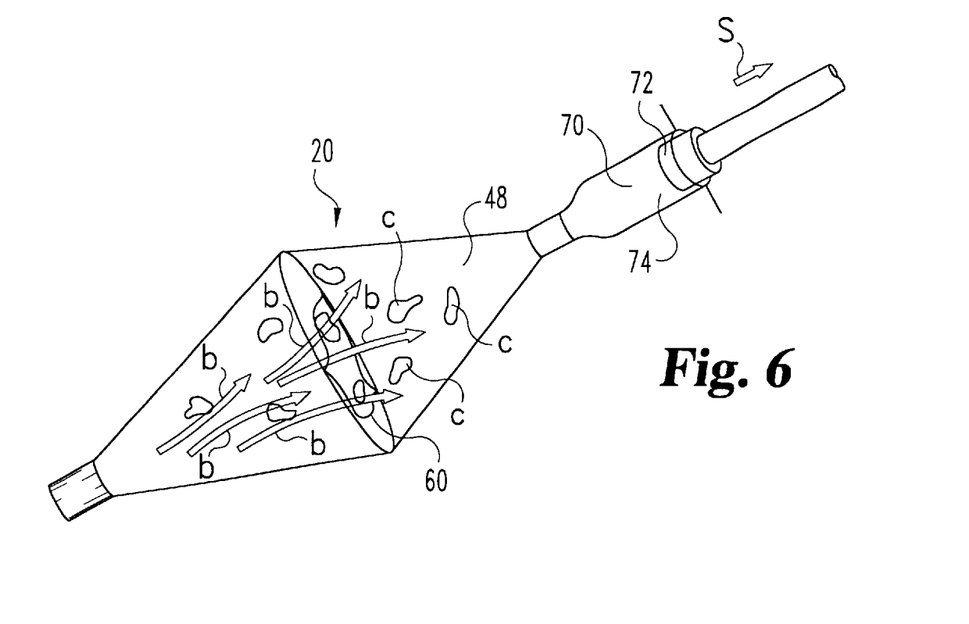
FIG. 6 is a side elevational view of a device of this invention in operation with the valve in the open position allowing blood and clot particles into the reservoir.

Suction force S provides sufficient pressure to open valve 60. In the particular embodiment shown in FIG. 6, as the piston 72 of the syringe 70 is withdrawn in the direction of arrow S, the valve 60 opens to allow blood and clots c to enter the reservoir 48 in the direction of arrows b. Blood and clot material may or may not enter the cylinder 74 of syringe 70. Any suitable suction means is contemplated. For example, an electric pump, suction bottle or other suitable device can be used in place of syringe 70.

Figure 7:
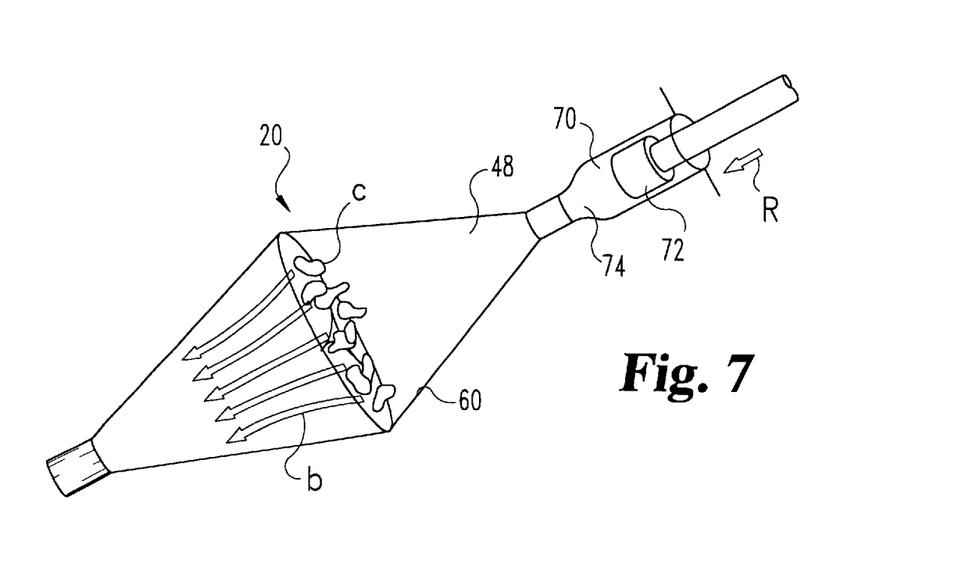
FIG. 7 is a side elevational view of the device shown in FIG. 1 with the valve in the closed position and trapping clot particles.

Once the suction force is removed, pressure is applied that is sufficient to push blood through the membrane along arrows b' but is not sufficient to deflect the leaflets in the direction of arrow R (FIG. 7). The pressure could be supplied by gravity or could be hydraulic pressure supplied by action of the syringe 70.

Figure 8:
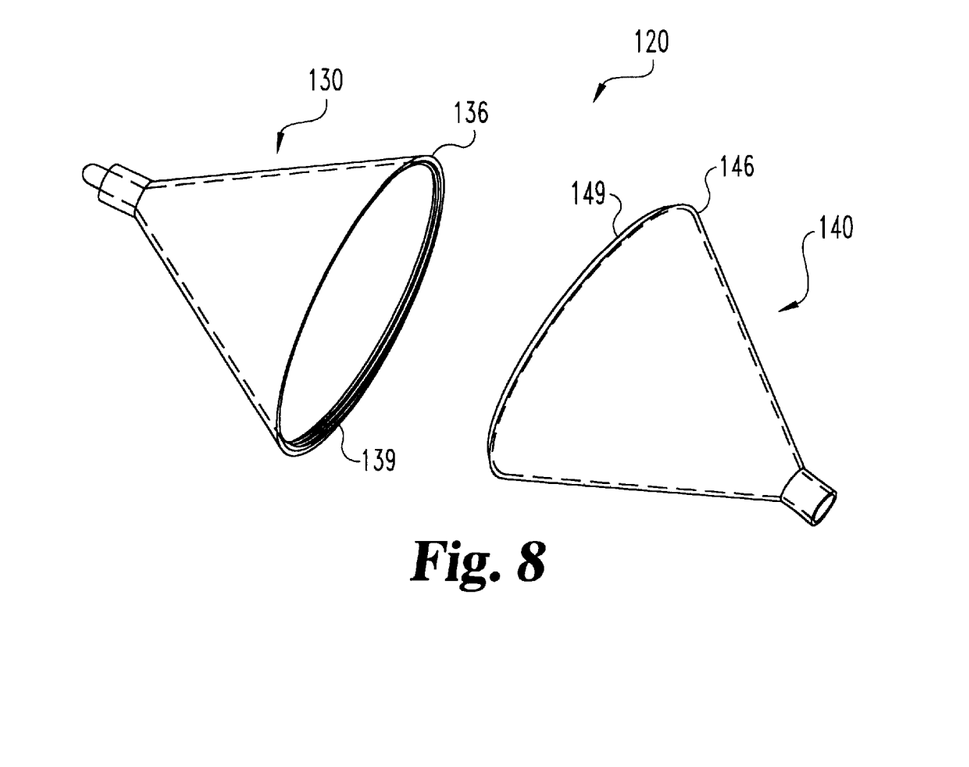
FIG. 8 is a side perspective view of housing portions of this invention that are engagable with screw threads.

The devices of the present invention are preferably disposable. In preferred embodiments, however, the housing portions 30, 40 are detachable so that the valve can be cleaned if needed during the procedure. Preferably, matable engagement members are disposed on the opposite ends of the housing portions. In the embodiment shown in FIG. 8, the opposite end 136 of the first housing portion 130 of device 120 defines a set of internal screw threads 139. The opposite end 146 of second housing portion 140 defines a set of external screw threads 149 that are matable with the internal screw threads 139. Any suitable arrangement is contemplated so long as the housing portions can be efficiently and easily engaged and disengaged.

Figure 9:
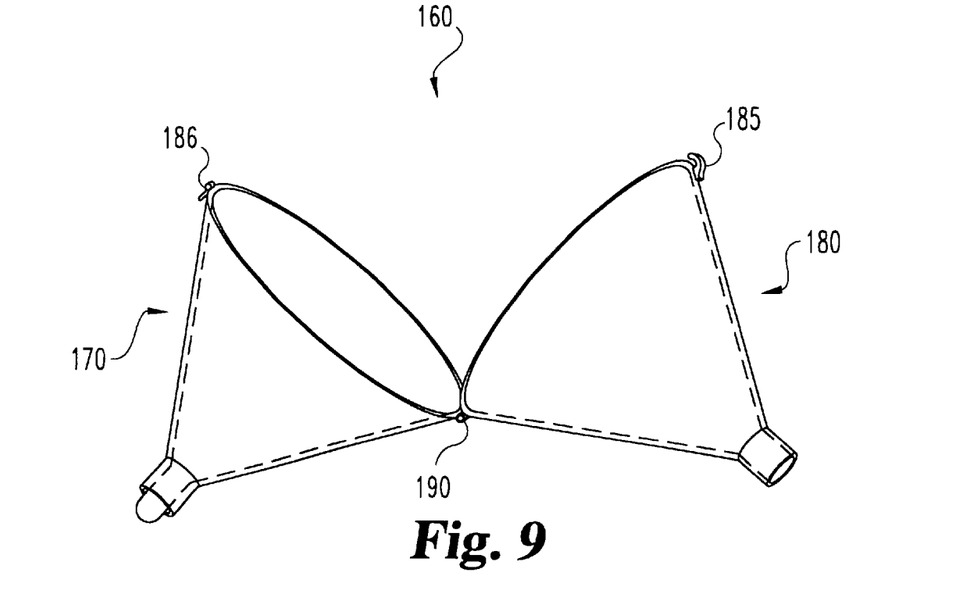
FIG. 9 is a side perspective view of a housing of this invention having a hinge and lock.

In another embodiment, the first and second housing portions 170, 180 of device 160 are partially detachable by way of a hinge and lock arrangement as shown in FIG. 9. Hinge 190 hingedly connects the first housing portion 170 to the second housing portion 180 so that device 160 can assume open and closed positions yet still remain attached. For example, the device 160 in FIG. 7 opens in a clam-shell type fashion. In the closed position, a lock assembly secures the device in the closed position. In the particular embodiment shown in FIG. 9 the lock assembly is a snap fastener having a knob 185, positioned or disposed on portion 180 and which engages a socket member 186 disposed at a corresponding location on portion 170. Any suitable locking mechanism is contemplated. For example, the lock assembly might include a Velcro fastener. The particular design of the lock member is not critical as long as lock member 185 revealingly engages the first housing portion 170 to the second housing portion 180.

The present invention also provides methods for removing a blood clot from a patient, separating blood clot particles from the patient's blood and salvaging the removed blood. The methods include providing a thromboaspiration catheter with a side arm port for suction and introducing the catheter into the blood vessel over a guide wire to make contact with or approach the thrombus. Typically, the thrombus is fragmented or reduced as is known in the art, such as with a device inserted through the hemostatic valve of the catheter device. A device of this invention is provided and the fluid port is engaged to the side arm port. A syringe or other suction device is engaged to the suction port of the device.

Suction pressure is applied from the suction device to the suction port of the device of present invention. The suction pressure is strong enough to open the valve and draw blood containing blood clot particles through the fluid port into the chamber and through the valve into the reservoir. The suction pressure is then removed causing the valve to assume the closed position and trap particles in the reservoir. Pressure is then applied by gravity or hydraulic pressure from ejection action of the syringe. The ejection pressure is sufficient to push blood through the membrane but insufficient to open the valve in the wrong direction.

In some cases, it is necessary to repeatedly remove, filter and return the blood. If the valve becomes full or clogged, the housing portions can be disengaged to access and clean the valve. This step can be performed while the assembly is still engaged to the patient.

Devices of any suitable size are contemplated by the invention. Preferably, the devices will range in diameter from about 1 cm to over 20 cm, with the most typical diameter being about 10 cm.

While the invention has been illustrated and described in detail in the foregoing description and examples, the same is to be considered as illustrative and not restrictive in character, it being understood that only the preferred embodiments have been shown and described, and that all changes and modifications that come within the spirit of the invention are desired to be protected.

What is claimed is:

1. A device for filtering blood clot particles from blood, compromising:

a housing having a first end defining a fluid port for fluid communication with the blood vessel system of a patient and an opposite end defining a suction port, the housing comprising a reservoir in fluid communication with the fluid port; and a valve disposed in said housing between said fluid port and said suction port, said valve comprising at least one semipermeable membrane member permeable to blood and impermeable to blood clot particles, said membrane member moveable to a first open valve position to permit passage of fluid and particles from said fluid port into said reservoir, and said membrane member movable to a second closed valve position to block passage of particles between said reservoir and said fluid port and to permit passage of blood through said membrane member to the fluid port for delivery to the patient.

2. The device of claim 1 wherein said membrane member includes at least one leaflet comprising a resilient material capable of deflecting to achieve the open position upon receiving suction pressure from said suction port and capable of returning to the closed position when suction is removed.

3. The device of claim 2 wherein said at least one leaflet comprises a plurality of valvate leaflets, each composed of a resilient material capable of deflecting to achieve the open position upon receiving suction pressure from said suction port and capable of returning to the closed position when suction is removed.

4. A device for filtering blood clot particles from blood, comprising:

a first housing portion having a first end defining a fluid port and an opposite end defining a first opening, said first housing portion defining a chamber in fluid communication with said fluid port and said first opening;

a second housing portion having a first end defining a suction port and an opposite end defining a second opening, said second housing portion defining a reservoir in fluid communication with said suction port and said second opening, said opposite end of said second housing portion hermetically sealingly engagable to said opposite end of said first housing portion; and a valve disposed between said chamber and said reservoir, said valve having an open position for allowing blood and blood clots to enter said reservoir from said chamber and a closed position preventing return of blood clots to said chamber, said valve including a plurality of leaflets disposed circumferentially adjacent to one another from an interior surface of one of said first housing portion and said second housing portion, at least one of said leaflets having a semipermeable membrane portion permeable to blood and impermeable to blood clot particles, at least one of said leaflets being composed of a resilient material capable of deflecting to achieve the open position upon receiving negative pressure from said suction port and capable of returning to the closed position when suction is removed.

5. The device of claim 4, further comprising a first engagement member disposed on said opposite end of said first housing portion and a second engagement member disposed on said opposite end of said second housing portion, said first engagement member matable with said second engagement member.

6. The device of claim 4 wherein said opposite end of said first housing portion defines a first set of screw threads and said opposite end of said second housing portion defines a second set of screw threads, said first set of screw threads matable with said second set of screw threads.

7. The device of claim 4 further comprising:

a hinge hingedly connecting said first housing portion to said second housing portion and a lock member revealingly engaging said first housing portion to said second housing portion.

8. A method for separating blood clot particles from blood, comprising:

providing a device of claim 1;

applying suction to the suction port to open the valve and draw blood containing blood clot particles through the chamber and into the reservoir; and removing suction form the suction port to close the valve and trap the particles within the reservoir.

9. A method of filtering blood clot particles from blood of a patient undergoing treatment for a thrombotic condition, comprising the steps of:

(a) providing a catheter having a side arm port for suction;

(b) introducing the catheter into a blood vessel;

(c) engaging the fluid port of a device of claim 4 to the side arm port;

(d) applying suction pressure to the suction port of the device to open the valve and draw blood containing blood clot particles through the valve into the reservoir;

(e) after drawing blood into the reservoir, removing the suction pressure to close the valve and trap particles in the reservoir.

10. The method of claim 9, further comprising the step of:

(f) reinjecting the blood from the reservoir into the patient through the catheter.

11. The method of claim 9 further comprising the step of:

(g) disengaging the first housing portion from the second housing portion and removing blood clot particles from the valve.

12. The method of claim 11 further comprising the step of:

(h) after removing blood clot particles from the valve, engaging the first housing portion to the second housing portion.

13. The method of claim 10 further comprising repeating steps (d) through (f) until the blood clot particles have been removed from the blood.

* * * * *